United States Patent [19]
Diedrich et al.

[11] Patent Number: 5,630,797
[45] Date of Patent: May 20, 1997

[54] EVERTING CATHETER SYSTEM AND METHOD OF UTILIZING THE SAME

[75] Inventors: Klaus Diedrich, Lubeck; Otmar Bauer, Kludenbach, both of Germany; Guy R. Lowery, Mission Viejo, Calif.; Steven R. Bacich, Laguna Niguel, Calif.; Hien V. Nguyen, Santa Ana, Calif.

[73] Assignee: Imagyn Medical, Inc., Laguna Niguel, Calif.

[21] Appl. No.: 372,970

[22] Filed: Jan. 17, 1995

[51] Int. Cl.$^6$ ........................................ A61M 31/00
[52] U.S. Cl. ........................ 604/55; 601/271; 601/280
[58] Field of Search ........................ 604/55, 271, 93, 604/158, 160, 164, 165, 161, 280, 264, 283, 905

[56] References Cited

U.S. PATENT DOCUMENTS

| | | |
|---|---|---|
| 4,243,040 | 1/1981 | Beecher ................................. 606/127 |
| 4,271,839 | 6/1981 | Fogarty et al. . |
| 4,946,440 | 8/1990 | Hall ...................................... 604/95 |
| 5,163,927 | 11/1992 | Woker et al. . |
| 5,171,305 | 12/1992 | Schickling et al. . |
| 5,300,023 | 4/1994 | Lowery et al. . |
| 5,346,498 | 9/1994 | Greelis et al. . |
| 5,374,247 | 12/1994 | Lowery et al. . |
| 5,389,100 | 2/1995 | Bacich et al. . |
| 5,472,419 | 12/1995 | Bacich . |
| 5,472,428 | 12/1995 | Peters ...................................... 604/171 |

*Primary Examiner*—Vincent Millin
*Assistant Examiner*—V. Alexander
*Attorney, Agent, or Firm*—Donald E. Stout

[57] ABSTRACT

An everting catheter system comprising an elongated outer tubular body having an outer body lumen and an opening leading from the outer body lumen, an elongated inner tubular body movable longitudinally in the outer body lumen and having an inner body lumen and an everting element coupled to the outer body and the inner body so that with movement of the inner body longitudinally in the outer body lumen the everting element can be everted and inverted. The system also includes an elongated instrument, such as a transfer catheter, movable longitudinally in the inner body lumen relative to the inner body. A coupling releasably couples the instrument to the outer body in a substantially fixed longitudinal position with respect to the outer body.

21 Claims, 6 Drawing Sheets

EVERTING CATHETER SYSTEM AND METHOD OF UTILIZING THE SAME

BACKGROUND OF THE INVENTION

In one treatment for infertility, biological material such as gametes, embryos and/or zygotes are deposited into the reproductive tract of a mammalian female. Application Ser. No. 08/053,150, now U.S. Pat. No. 5,374,247 describes a technique for delivering a substance, such as biological material, to the fallopian tube utilizing an everting catheter and a transfer or delivery catheter.

It is also known to deposit biological material in the uterus. The uterus comprises opposed walls which are either in contact or in closely adjacent confronting relationship.

A transfer catheter can be used to deposit a substance in the uterus. It would be desirable to use an everting catheter to place the transfer catheter in the uterus because of the atraumatic nature of the everting catheter. A known everting catheter includes an elongated outer tubular body having an outer body lumen, an opening leading from the outer body lumen, an elongated inner tubular body movable longitudinally in the outer body lumen and having an inner body lumen, and an everting element coupled to the outer body and the inner body. Consequently, with movement of the inner body longitudinally in the outer body lumen, the everting element can be everted and inverted.

Everting of the everting catheter within the uterus urges the opposed walls of the uterus apart to form a chamber. The transfer catheter can then be inserted into the everting catheter to place the distal end of the transfer catheter at or closely adjacent the distal end of the everted everting element. However, the distal end of the transfer catheter may be occluded by being pressed into the endometrial tissue and delivery of the substance through the transfer catheter when in this position may be difficult if the distal opening of the transfer catheter is occluded by the everting element. The consequence of this occlusion is that the deposition of biological material, which may comprise only a few cells, will not occur if the biological material remains in the lumen of the inner body.

It is also possible to use an everting catheter to place a sampling instrument within a location, such as the urinary bladder, in the human body. In this event, it is desirable to know the location of the sampling instrument and to have the sampling instrument held in a stable condition.

SUMMARY OF THE INVENTION

This invention facilitates the deposition of a substance in the uterus. This is accomplished in part by providing for forward advancement of a transfer catheter or an instrument without shear forces of the transfer catheter or instrument against the inner walls of the uterus. Everting of the everting element provides a lumen in which to advance the transfer catheter or instrument. Once at the distal end of the inner lumen of the everting element, the distal end of the transfer catheter or instrument can be exposed by inverting the everting element sufficiently to provide a peel back condition of the everting element in which the distal end portion of the transfer catheter extends distally of the everting element and is in the chamber of the uterus which is formed by urging of the opposed walls of the uterus apart. The substance is then delivered through the transfer catheter to the uterus when the everting element is in the peel back condition. In order to provide the peel back condition, it is only necessary that the inversion of the everting element move the distal end of the everting element proximally sufficiently relative to the distal end of the transfer catheter so as to adequately expose the distal opening of the transfer catheter.

This method may be carried out in other parts of the reproductive tract such as the fallopian tubes, or in other procedures in other interior regions of a patient's body. In a broader sense, the method of this invention may be used in transferring a substance in either direction between an interior body region of a patient and a location outside the body of the patient. The features of this invention may also be used with instruments other than a transfer catheter.

The everted everting element tends to grip the transfer catheter as described, for example, in Lowery et al U.S. Pat. No. 5,300,023. Consequently, inverting of the everting element tends to pull the transfer catheter proximally. With this invention, the transfer catheter is retained against proximal movement sufficiently to provide the peel back condition referred to above. Although the transfer catheter may be manually retained against proximal movement, preferably a coupling is used to mechanically couple the transfer catheter to the outer body of the everting catheter. Although various substances can be deposited, typically the substance is biological material, such as gametes, embryos or zygotes.

The distal end portion of a transfer catheter typically has a distal opening at the distal end of the catheter through which a substance can pass from the interior of the transfer catheter to the exterior of the transfer catheter. The everted balloon not only tends to grip the distal end portion of the transfer catheter but also may cover or partly cover and therefore occlude or partially occlude the distal opening of the transfer catheter. However, in the peel back condition of the everting element, the distal opening of the transfer catheter is in the chamber formed by the everting element and is located distally of the everting element. In other words, in the peel back condition, the distal opening of the transfer catheter is not occluded by the everting element and is less likely to be occluded by tissue in that it is located in the chamber formed by the eversion of the everting element. Also, because the distal opening is not within the everting element or inner body lumen, it is more likely that all of the substance to be deposited will be deposited in the uterus. Accordingly, the substance can flow relatively freely from the interior of the transfer catheter through the distal opening of the transfer catheter into the chamber of the body region. Importantly, the distal end opening of the transfer catheter can be placed into the chamber of the uterus without forward shear forces against the uterine walls. This also will provide for less trauma to the delicate uterine lining and less likelihood of collecting material or mucus in the distal end opening of the transfer catheter.

To accomplish this, the coupling preferably couples the transfer catheter to the outer body in a substantially fixed longitudinal position with respect to the outer body. The coupling need not lock the transfer catheter to the outer body in the substantially fixed longitudinal position. Preferably, the coupling merely detents or releasably retains the transfer catheter in the substantially fixed longitudinal position.

The coupling may be of virtually any construction that will suitably retain the transfer catheter. For example, the coupling may include a clip coupled to the outer body and releasably couplable to the transfer catheter. In a preferred construction, the coupling includes an elongated handle coupled to the outer body and releasable attachment portions on the transfer catheter and the handle for releasably retaining the transfer catheter in the substantially fixed longitudinal position. By providing the handle with a longitudinal handle passage in communication with the outer body lumen, the transfer catheter can be received in the handle passage.

Another feature of the invention is that the attachment portions are responsive to movement of the transfer catheter to bring the attachment portion of the transfer catheter to the attachment portion of the handle to retain the transfer catheter in the substantially fixed longitudinal position. Conversely, movement of the inner body proximally can be used to decouple the transfer catheter from the outer body. This can be accomplished with only one hand of the operator.

In a preferred construction, the handle has an elongated longitudinally extending slot and the attachment portion of the transfer catheter is slidable in the slot. The attachment portion of the handle can advantageously include one or more recesses in the handle and the attachment portion of the transfer catheter preferably includes an enlarged member receivable within the recess.

The handle provides other advantageous functions. For example, the everting catheter may include an inner body fitting coupled to the proximal end portion of the inner body and the inner body fitting is slidable in the handle passage and in the slot to thereby mount the inner body fitting for movement. Thus, the handle guides the movement of the inner body fitting to facilitate its movement. By having a projecting portion of the inner body fitting project out of the slot, manual longitudinal movement of the inner body fitting in the slot is facilitated.

The coupling for coupling the instrument to the outer body in a substantially fixed longitudinal position with respect to the outer body may include certain structure on the transfer catheter as well as means on the outer body cooperable with the transfer catheter for retaining the transfer catheter in the inner body lumen in the substantially fixed longitudinal position. This coupling and such means may take various other forms. For example, a spring biased detent, or a lock which includes a pin and a slot as well as various snap-fit devices may be employed. A deformable tube may be squeezed against a slidable member to achieve the desired releasable coupling and twist or rotatable locks may be used.

Various features of this invention are applicable to performing various different procedures in the interior body region of a patient whether or not a peel back condition is provided. One example of such a procedure is obtaining a sample of tissue, fluid or other substance from an interior body region, such as the urinary bladder. In this event, there is no need to provide a peel back condition. However, by releasably retaining the instrument in a substantially fixed longitudinal position relative to the outer body of the everting catheter the instrument, in this case a sampling instrument, can be properly positioned and stably retained. This can advantageously be accomplished by coupling the instrument to the handle. The procedure, such as taking a sample, can then be performed while the instrument is coupled to the handle. Thus, the handle is useful whether or not the everting catheter is used in a procedure which includes providing the peel back condition. Another example of a procedure which may not require peel back is delivering a substance to the interior body region.

When the everting catheter is to be used in the uterus, the outer body may have a curved distal end portion. In addition, the everting catheter may include a cervical disk on the distal end portion of the outer body.

This invention also provides a novel transfer catheter which includes a catheter body and a member coupled to the catheter body between the proximal and distal ends of the catheter body and spaced from both of such ends. The member includes a slide at least partially surrounding the catheter body for use in mounting the catheter body for sliding movement, a manipulator adapted for manual manipulation and a neck joining the slide to the manipulator. The neck can be narrower than the slide. In a preferred construction, the neck is also narrower than the manipulator so that the member has generally opposed grooved portions. The transfer catheter also preferably includes a proximal fitting coupled to the catheter body proximally of the member with the member being closer to the proximal end than to the distal end of the catheter body.

The invention, together with additional features and advantages thereof may best be understood by reference to the following description taken in connection with the accompanying illustrative drawings.

DESCRIPTION OF THE PREFERRED EMBODIMENT

Figures 1, 6, 7:
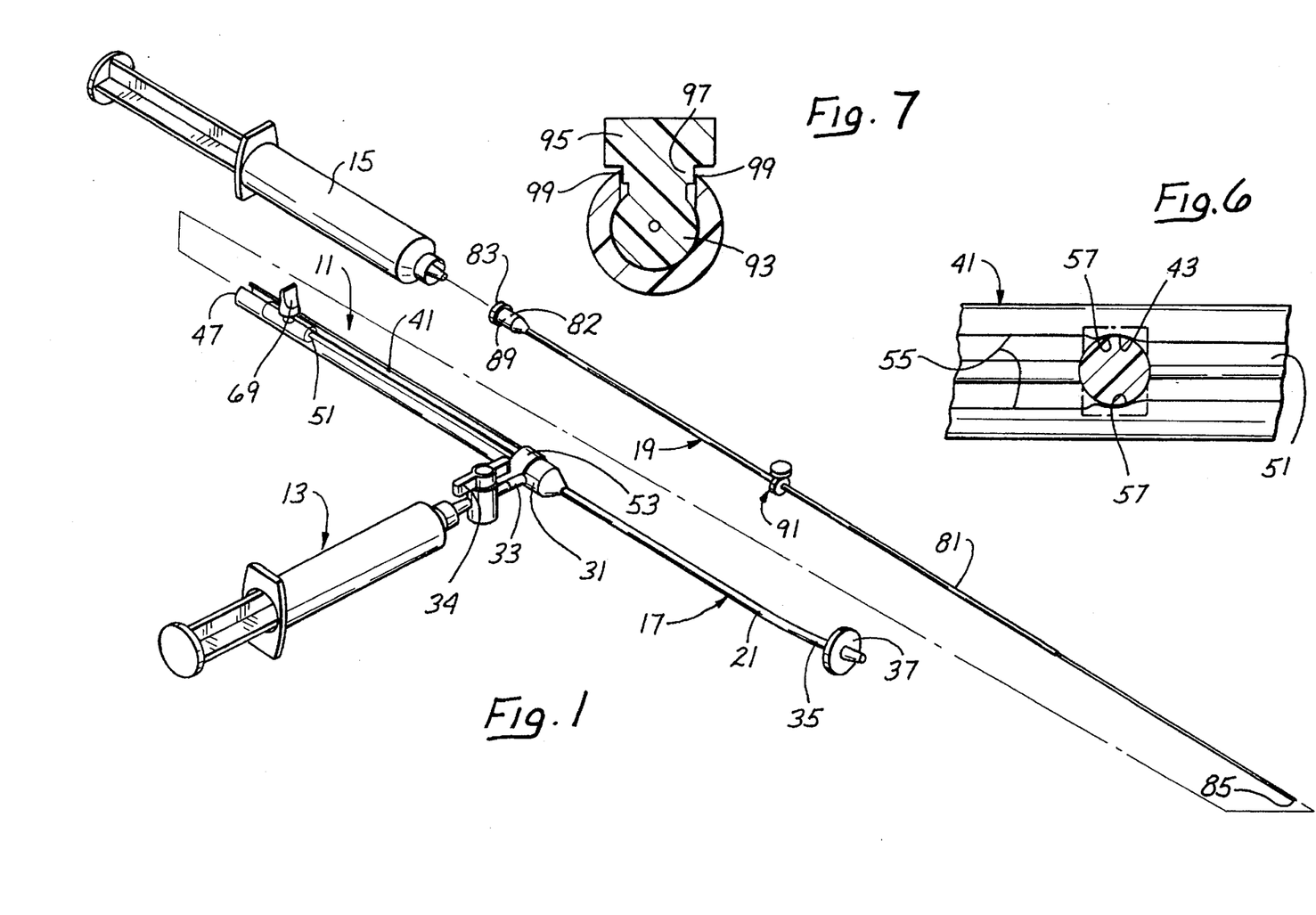
FIG. 1 is a perspective view of an everting catheter system constructed in accordance with the teachings of this invention and of syringes for use with such system.
FIG. 6 is a fragmentary plan view partially in section taken generally along line 6—6 of FIG. 4.
FIG. 7 is a sectional view taken generally along line 7—7 of FIG. 4.

FIG. 1 shows an everting catheter system 11 coupled to a syringe 13 and adapted to be coupled to a transfer catheter syringe 15. Generally, the everting catheter system 11 includes an everting catheter 17 and an instrument, which in this embodiment is a transfer catheter 19.

The everting catheter 17 includes an elongated outer tubular body 21 (FIGS. 1, 3 and 3A) having an outer body lumen 23, an elongated inner tubular body 25 movable longitudinally in the outer body lumen 23 and having an inner body lumen 27 adapted to receive the transfer catheter 19 (FIG. 4A), and a flexible everting element 29 coupled to the outer body and inner body. Accordingly, with movement of the inner body 25 longitudinally in the outer body lumen 23, the everting element 29 can be everted and inverted. Everting catheters of this general type are well known and are disclosed, for example, in Woker et al U.S. Pat. No. 5,163,927, Lowery et al U.S. Pat. No. 5,300,023 and Schickling et al U.S. Pat. No. 5,171,305.

Figure 3:
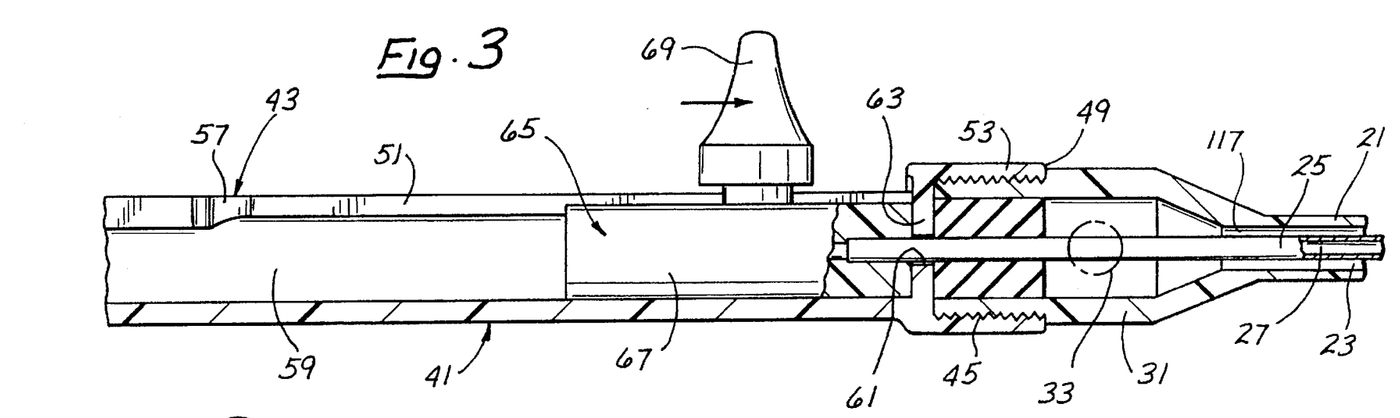
FIG. 3 is an enlarged, fragmentary, longitudinal sectional view illustrating the handle and proximal regions of the everting catheter in the everted condition.

In this embodiment, the outer body 21 is formed integrally with an outer body fitting 31 which is larger radially than the major length of the outer body 21 and which is provided at a proximal end portion of the outer body. If desired, the outer body fitting 31 can be a separate member attached to the outer body 21 in accordance with conventional techniques. The outer body fitting 31 has a radially extending leg 33 (FIG. 1) which communicates through a valve 34 with the interior of the outer body as shown in FIG. 3.

The outer body 21 has a curved distal end portion 35 to facilitate alignment of the distal end portion 35 with the cervix. In addition, a cervical disc 37, which may be conventional (FIGS. 1–2A), is attached to the distal end portion 35 at a location spaced slightly proximally from a distal end 39 of the outer body 21. The cervical disc 37 has a conical protruding section 40 and a transparent or translucent flange 42 to enable visualization through the flange.

Although various biocompatible materials may be utilized, in this embodiment the outer body 21 is constructed of a polymeric material such as polyethylene or polypropylene and the inner body 25 is preferably constructed of a metal such as stainless steel with a polypropylene liner. Both the outer body 21 and the inner body 25 are relatively rigid to adapt the everting catheter 17 for gaining transcervical access to the uterus. However, for other applications, the bodies 21 and 25 may be more flexible, if desired.

Figure 4:
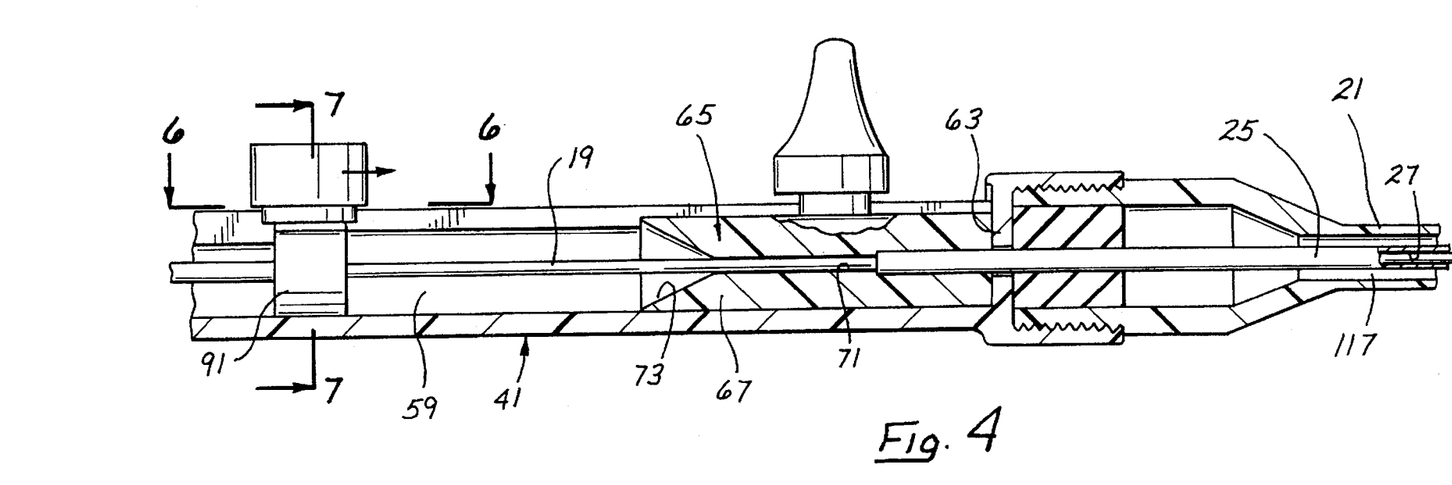
FIG. 4 is a view similar to FIG. 3 illustrating the transfer catheter in the substantially fixed longitudinal position.
Figure 4A:
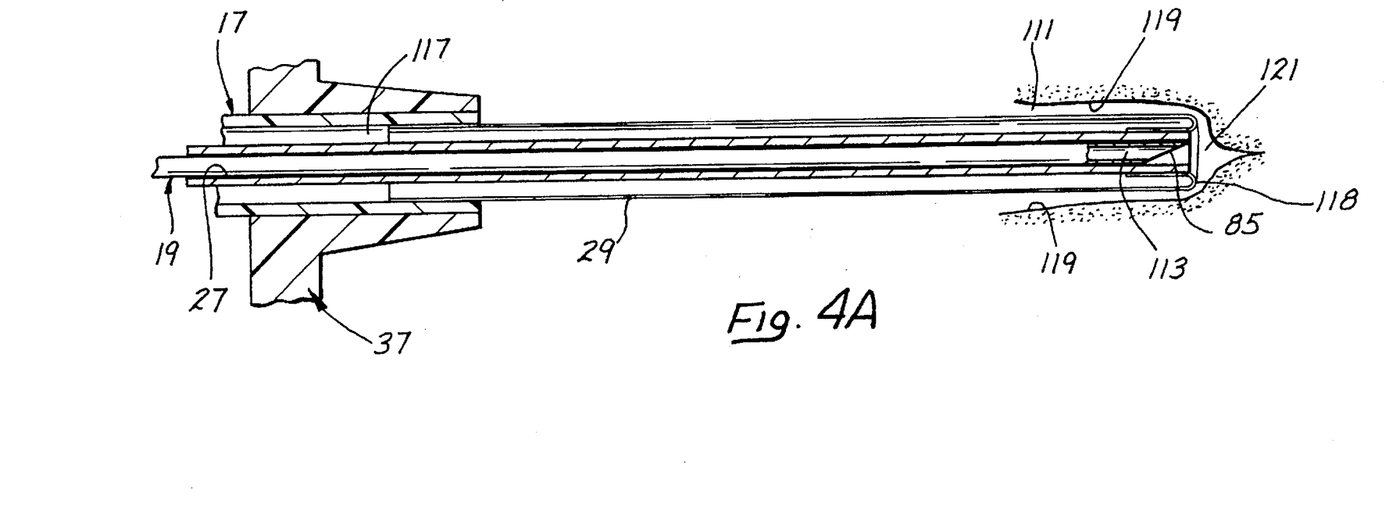
FIG. 4A is a view similar to FIG. 3A illustrating the transfer catheter in the same position as shown in FIG. 4.

As described more fully below, the transfer catheter 19 is receivable within the inner body lumen 27 (FIG. 4A). The everting catheter 17 includes means on the outer body 21 cooperable with the transfer catheter 19 for retaining the transfer catheter in the inner body lumen 27 in a substantially fixed longitudinal position relative to the outer body. Although such means can take various different forms as discussed above, in this embodiment such means includes an elongated handle 41 (FIGS. 1, 3 and 6) coupled to the outer body 21 and an attachment portion 43 on the elongated handle cooperable with the transfer catheter for retaining the transfer catheter in the substantially fixed longitudinal position. The handle 41, which can be coupled to the outer body fitting 31 by screw threads 45 (FIG. 3) has a proximal end 47 (FIG. 1), a distal end 49 (FIG. 3) and an elongated slot 51 extending axially from the proximal end of the handle distally for a major length of the handle. In this embodiment, the handle 41 has a distal threaded socket 53 which receives a region of the outer body fitting 31, and the slot 51 extends all the way to the socket. As best seen in FIG. 6, the handle 41 has generally opposed surfaces 55 which define the slot 51, and although the attachment portion 43 may be of various different constructions, in this embodiment the attachment portion 43 includes generally opposed recesses 57 provided in the surfaces 55. The recesses 57 are spaced proximally from the distal end 49 of the handle 41 and from the socket 53. In addition, the slot 51 narrows at the recesses 57 such that the slot 51 distally of the recesses is narrower than the slot 51 proximally of the recesses.

The handle 41 can advantageously be in the form of an elongated, substantially cylindrical tube of a suitable rigid polymeric material such as an acrylic. The handle 41 has a longitudinal handle passage 59 communicating with the outer body lumen 23. The handle passage 59, which is generally cylindrical in this embodiment, extends from the proximal end 47 of the handle 41 axially completely through the handle. The handle passage 59 is reduced to a relatively small opening 61 (FIG. 3) at a transverse wall 63. The slot 51 communicates with the passage 59 as shown in FIG. 3. The handle 41 is rigid and sufficiently long so that it can be easily manually grasped.

The everting catheter 17 also includes an inner body fitting 65 coupled to a proximal end portion of the inner body 25. The inner body fitting 65 is slidable in the handle passage 59. More specifically, the inner body fitting 65 includes a slide portion 67 having a generally cylindrical periphery sized to slide longitudinally within the handle passage 59 and a projecting portion 69 which projects through the slot 51 radially outwardly to facilitate manual longitudinal movement of the inner body fitting in the handle passage 59. The slide portion 67 has an axial passage 71 (FIG. 4) extending completely through it and a conical lead in taper 73 at the proximal end of the passage 71 to facilitate insertion of the transfer catheter 19 into the passage 71. The passage 71 communicates with the inner body lumen 27. The recesses 57 (FIGS. 3 and 6) are spaced proximally of the distal end 49 of the handle 41 sufficiently to permit some longitudinal movement of the projecting portion 69 along the slot 51 and to permit the projecting portion to be located distally of the recesses. The inner body fitting 65 can be constructed of any suitable material with a polymeric material such as polyethylene.

The transfer catheter 19 includes an elongated, flexible catheter body 81 and a proximal fitting 82. The catheter 19 has a proximal opening 83 at a proximal end of the transfer catheter, a distal opening 85 at a distal end of the transfer catheter and a lumen 87 (FIG. 5A) extending between the proximal and distal openings. The proximal fitting 82 (FIG. 1) is coupled to the proximal end of the catheter body and provides the proximal opening 83. Preferably, although not necessarily, the distal end of the transfer catheter 19 is cut at a bias angle as shown by way of example in FIG. 5A. The catheter body 81 is sized to extend into the everting catheter 17, to be received within the inner body lumen 27 and to be received in the reproductive tract of a mammalian female.

A member 91, which is enlarged relative to the cross section of the catheter body 81, is coupled to the catheter body 81 between the proximal and distal ends of the catheter body and is spaced from such proximal and distal ends. The member includes a slide 93 (FIG. 7) of part circular configuration and of a size and shape to be slidably received within the handle passage 59. The slide 93 at least partially surrounds the catheter body 81, and in this embodiment, completely surrounds the catheter body so that the slide mounts the catheter body for sliding movement in the handle passage 59.

The member 91 also includes a manipulator 95 adapted for manual manipulation so that the catheter body 81 can be moved longitudinally in the handle passage 59. The member 91 also includes a neck 97, which is narrower than the slide 93. In this embodiment, the neck 97 is also narrower than the manipulator 95 such that the member is provided with generally opposed groove portions 99 (FIG. 7). The neck 97 slides loosely in the relatively wide proximal region of the slot 51 and is guided more snugly in the narrower distal region of the slot 51. In this embodiment, the groove portions 99 form releasable attachment portions cooperable with the recesses 57 for releasably retaining the transfer catheter 19 in a substantially fixed longitudinal position.

The member 91 is preferably positioned closer to the proximal end of the catheter body 81 than to the distal end of the catheter body 81. The recesses 99 of the transfer catheter 19 are slidable longitudinally in the slot 59 proximally of the recesses 57 (FIGS. 6 and 7.)

Figure 2:
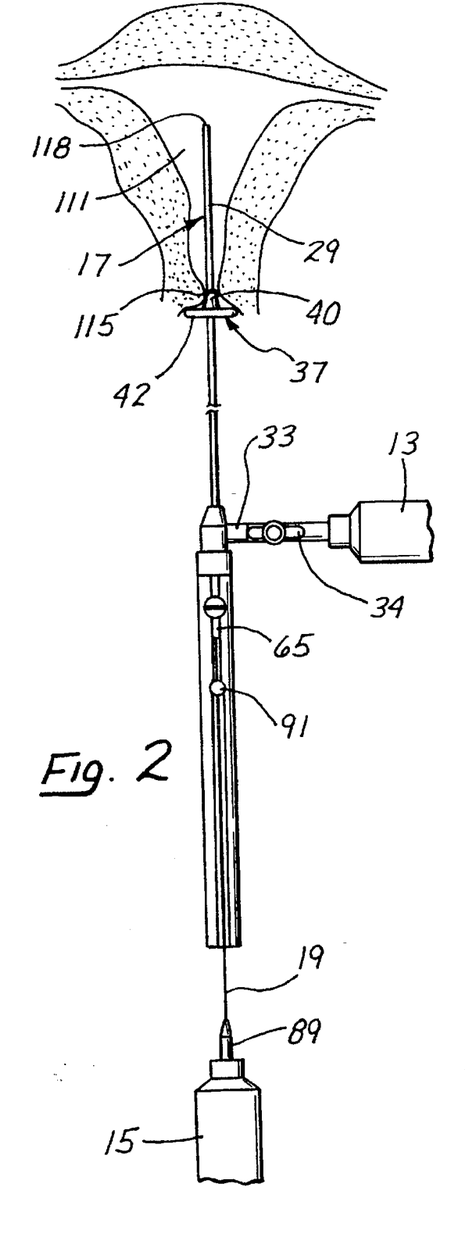
FIG. 2 is fragmentary elevational view illustrating the everting catheter system in use with the everting element everted within the uterus.
Figure 3A:
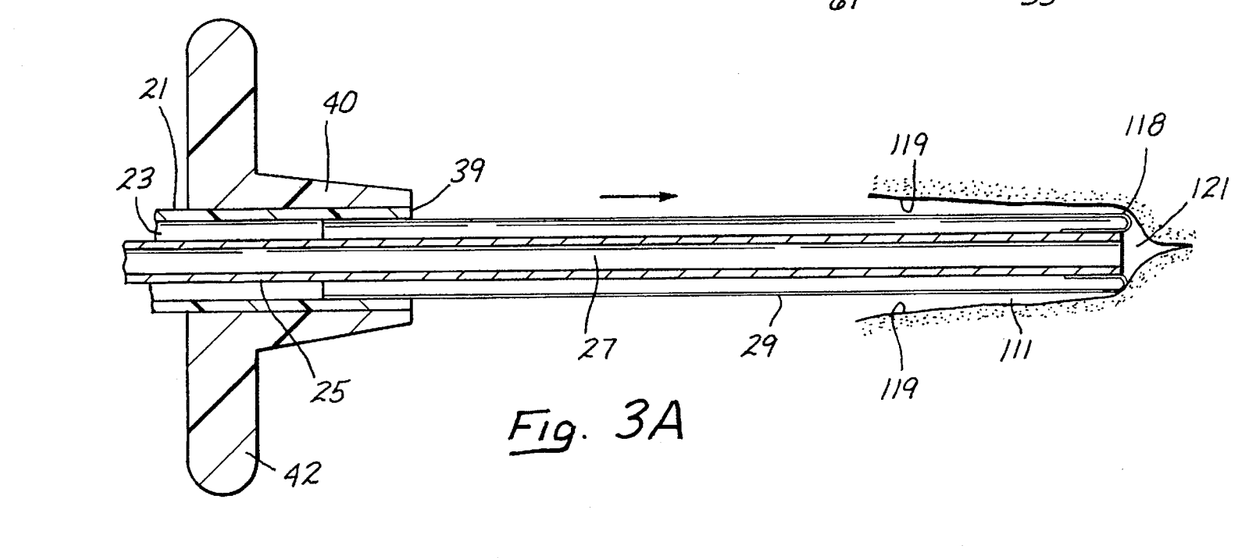
FIG. 3A is an enlarged fragmentary sectional view illustrating the everting element everted in the uterus.

The everting catheter system 11 can be used in transferring of a substance between an interior body region of a patient and a location outside the body of the patient. This is illustrated by way of example in FIGS. 2–5A with reference to the reproductive tract of a mammalian female, specifically the uterus 111 of a human patient. With reference to FIG. 2, the everting catheter 17 is provided at a location in the uterus 111 with the everting element 29 being everted as shown in FIG. 3A and with the transfer catheter 19 extending through a substantial length of the everting catheter and having a distal end portion 113 (FIG. 4A) within the everting element 29. Although this can be brought about in different ways, preferably it is accomplished by obtaining transcervical access to the uterus 111, and this can be accomplished in accordance with known techniques. For example, with the everting element 29 completely inverted, the everting catheter 17 can be inserted through the vagina and the cervix 115 (FIG. 2) until the protruding section 40 of the cervical disc 37 passes through the cervix and the flange 42 prevents further entry of the everting catheter. Thereafter, the everting element 29 can be everted by expelling an appropriate liquid from the syringe 13 through the leg 33 (FIGS. 1 and 3) to an annular gap 117 (FIGS. 4 and 4A) between the outer body 21 and the inner body 25 while the inner body is moved distally by the operator pushing with the operator's thumb on the projecting portion 69 of the inner body fitting 65. The eversion of the everting element 29 continues until the inner body fitting 65 abuts the transverse wall 63 as shown in FIG. 4 to thereby define a known position of the distal end 118 of the everting element 29 and of the everting catheter 17.

The uterus 111 includes opposed walls 119 (FIGS. 3A, 4A and 5A) which normally lie in closely adjacent confronting relationship. The eversion of the everting element 29 in the uterus 111 tends to urge the opposed walls 119 apart to form a chamber 121 as shown in FIGS. 3A, 4A and 5A.

The transfer catheter 19 can then be inserted through the passage 71 of the inner body fitting 65 and the inner body lumen 27 until the distal opening 85 is substantially at the distal end of the everting catheter 17. In this position, the distal opening 85 is within the everting catheter. It is preferred not to extend the distal end of the transfer catheter 19 distally of the distal end of the everting catheter 17 because it may injure the walls 119 of the uterus 111. Thus, the distal opening 85 and the distal end of the transfer catheter 19 are within the everting element 29 as shown for example in FIG. 4A.

More specifically, the transfer catheter 19 is sized in relation to the everting catheter 17 such that with the distal end of the transfer catheter in the position of FIG. 4A, the member 91 is received within the recesses 57 to releasably mechanically couple the transfer catheter 19 to the outer body 21 in a substantially fixed longitudinal position with respect to the outer body. The recesses 57 and the member 91 provide, in effect, a coupling for achieving this releasable coupling feature. The coupling is responsive to movement of the transfer catheter 19 distally to substantially the fixed longitudinal position to releasably couple the transfer catheter to the outer body 21 in the substantially fixed longitudinal position. This substantially fixed longitudinal position of the transfer catheter 19 is shown in FIGS. 4 and 4A. With the inner body fitting 65 abutting the transverse wall 63 and the member 91 releasably received by the recesses 57, the transfer catheter 19 and the everting catheter 17 are in the position shown in FIGS. 4 and 4A.

Figure 5:
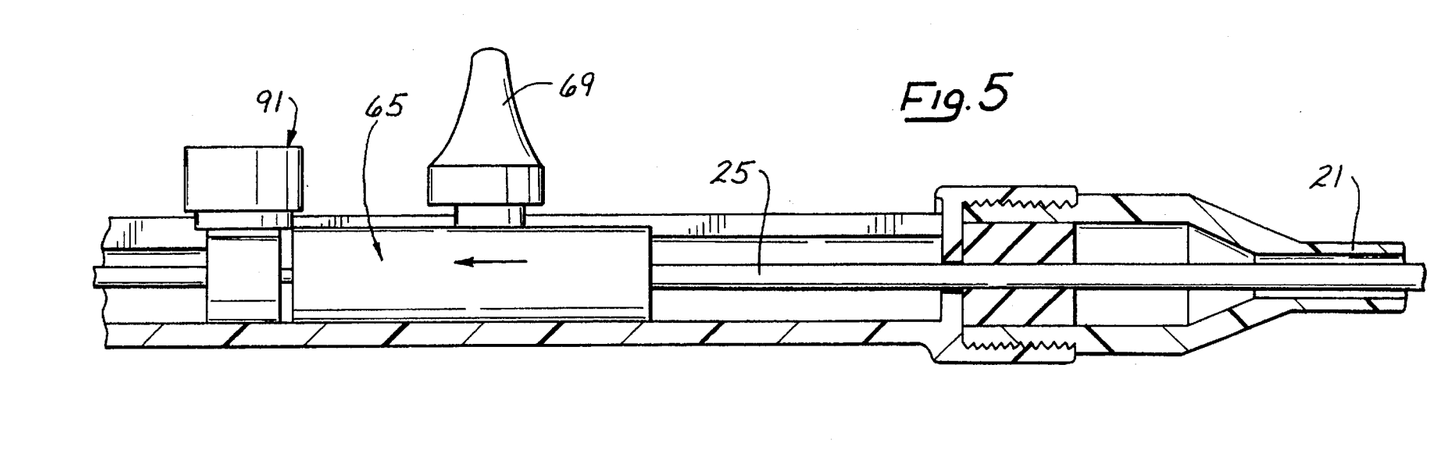
FIG. 5 is a view similar to FIG. 3 illustrating the components in the position which they assume in the peel back condition.
Figure 5A:
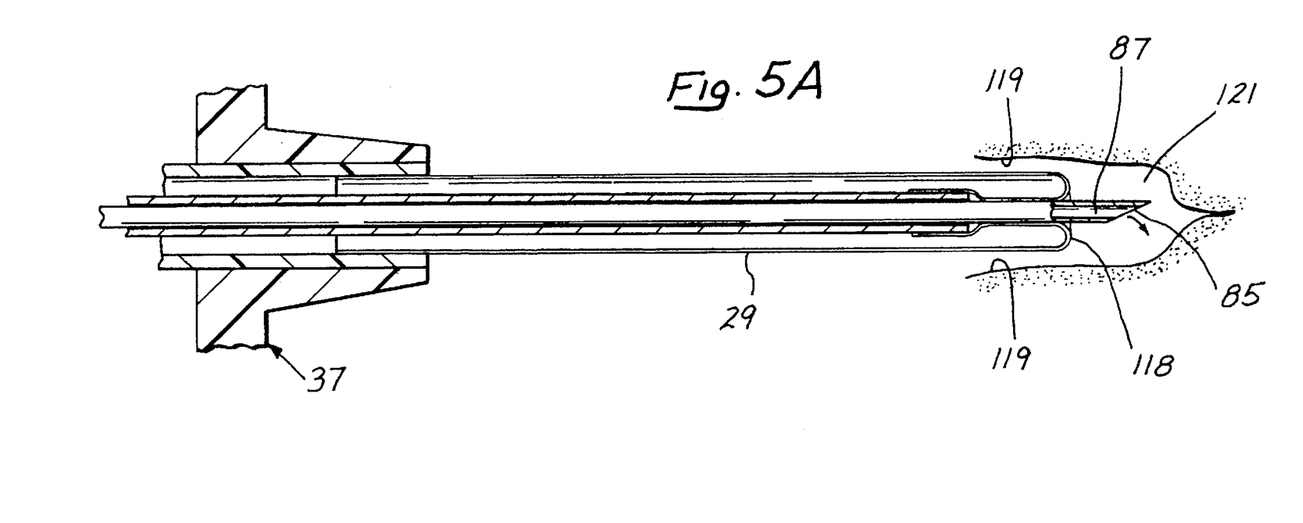
FIG. 5A is a view similar to FIG. 3A illustrating the peel back condition.

Next, the everting element 29 is inverted by manually moving the inner body fitting 65 proximally as shown in FIG. 5. During this proximal movement of the inner body fitting 65 and the inversion of the everting element 29, the transfer catheter 19 is retained against proximal movement sufficiently to provide a peel back condition of the everting element 29 (FIGS. 2A and 5A) in which the distal end portion of the transfer catheter, and in particular the distal opening 85, extend or lie distally of the distal end 118 of the everting catheter 17. In the peel back condition the distal opening 85 of the transfer catheter is in the chamber 121 and the distal opening 85 is not in the inner body lumen 27 or the everting element 29 and is not occluded or partially occluded by the everting catheter 17.

Figure 2A:
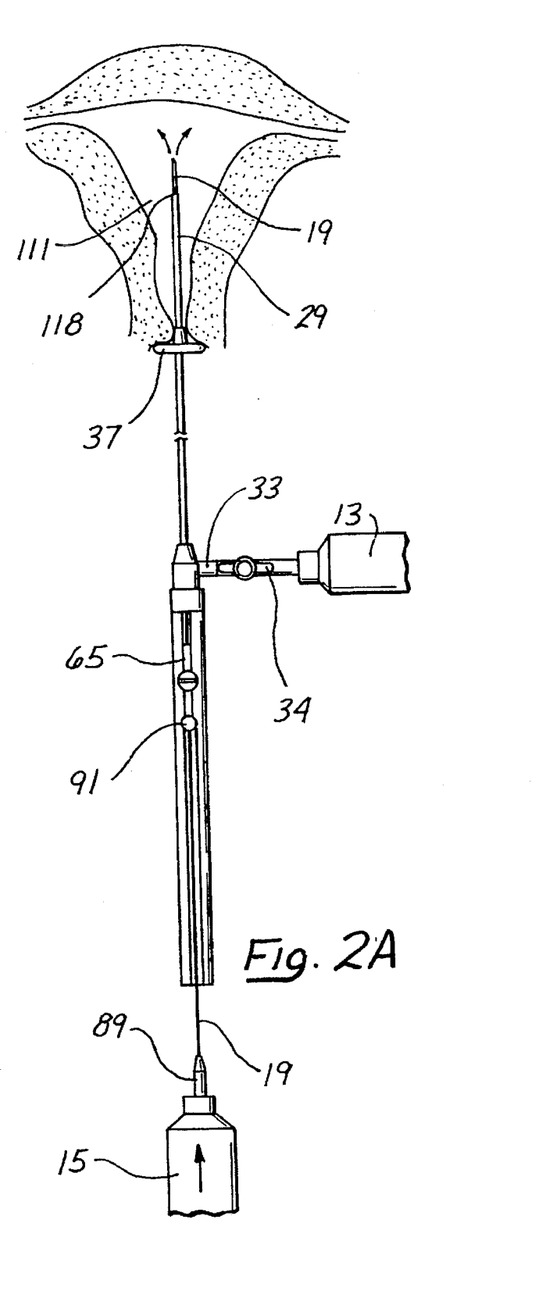
FIG. 2A is a view similar to FIG. 2 showing the peel back condition of the everting element.

The inversion of the everting element 29 causes the everting element to grip the transfer catheter 19 and tend to pull it proximally. However, releasable coupling formed by the member 91 and the recesses 57 of the handle 41 are sufficient to hold the transfer catheter 19 against proximal movement and in the substantially fixed longitudinal position during inversion. Next, the desired substance, which may be biological material such as gametes, embryos or zygotes is passed through the transfer catheter to the chamber 121 when the everting element 129 is in the peel back condition of FIG. 5A. This step of passing may be accomplished by, for example, drawing of the biological material into the syringe 15, coupling the syringe 15 to the proximal fitting 89 of the transfer catheter 19 and forcing the biological material through the transfer catheter utilizing the syringe 15 as shown in FIG. 2A. In most instances, the biological material will be preloaded prior to insertion through inner body fitting 65.

Upon completion of the deposition of the biological material into the uterus 111, the operator moves the inner body fitting 65 further proximally into contact with the member 91 to remove it from the recesses 57 to thereby decouple the transfer catheter 19 from the outer body 21. Thus, the coupling formed by the member 91 and the recesses 57 is responsive to movement of the inner body 65 proximally to a predetermined location to decouple and to allow movement of the transfer catheter relative to the outer body. This can be accomplished with only one hand.

Figures 8, 9, 10:
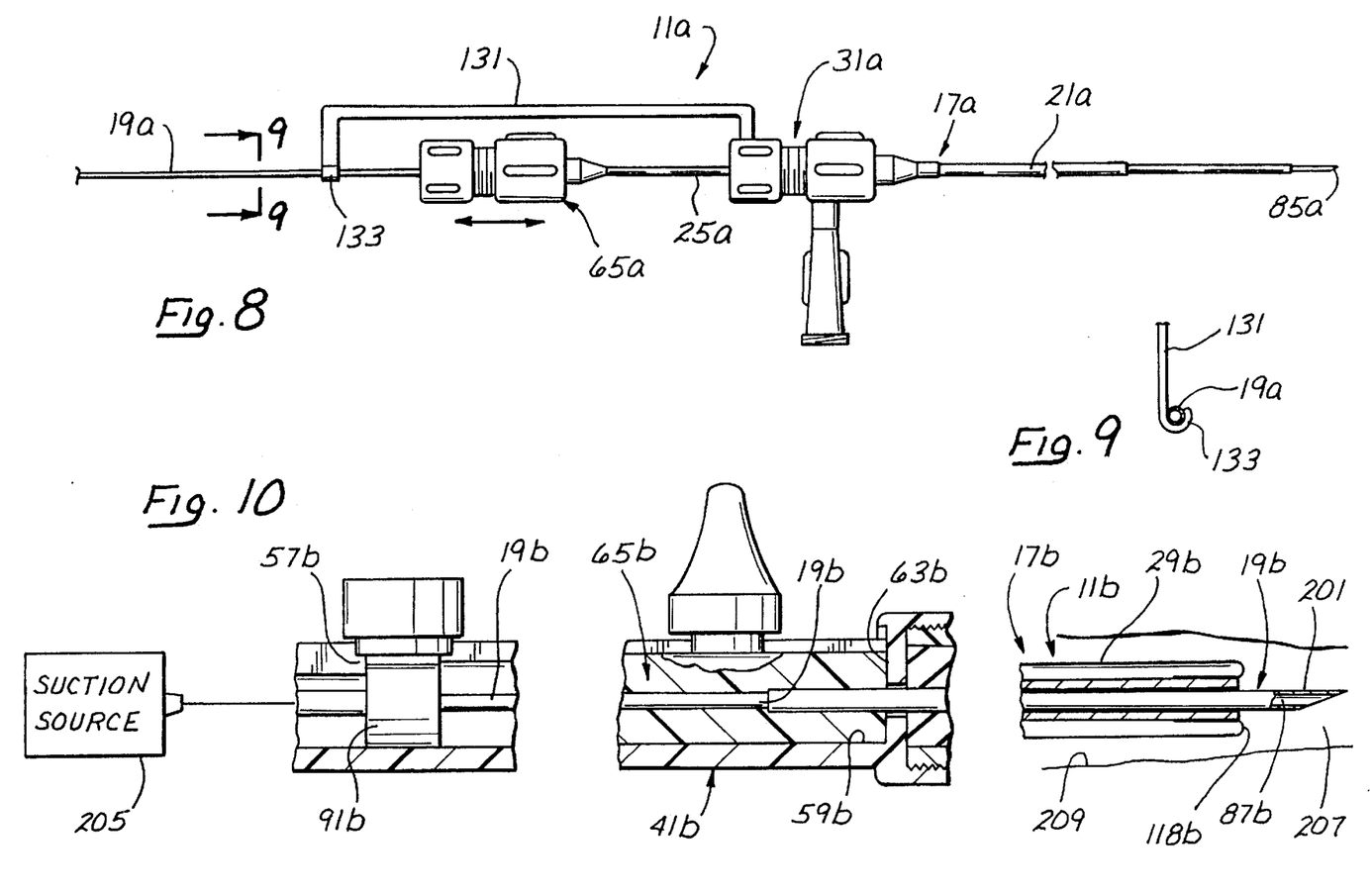
FIG. 8 is an elevational view of a second embodiment of everting catheter system constructed in accordance with the teachings of this invention.
FIG. 9 is an elevational view partially in section taken generally along line 9—9 of FIG. 8.
FIG. 10 is a schematic illustration showing use of the everting catheter system in taking a sample from the urinary bladder.

FIGS. 8 and 9 show an everting catheter system 11a which is identical to the everting catheter system 11 in all respects not shown or described herein. Portions of the everting catheter system 11a corresponding to portions of the everting catheter system 11 are designated by corresponding reference numerals followed by the letter a.

A primary difference between the systems 11 and 11a is that the latter includes a clip 131 coupled to the outer body 21a by the outer body fitting 31a and releasably coupled to the transfer catheter 19a. As shown in FIG. 9, the clip 131, which may be constructed of a suitable metal or polymeric material, has a cradle 133 of resilient material into which a region of the transfer catheter 19a may be forced. The cradle 133 resiliently grips the transfer catheter 19a with sufficient force to retain the transfer catheter in a substantially fixed longitudinal position with respect to the outer body 21a. Thus, the transfer catheter 19a is held against proximal movement sufficiently to provide the peel back condition discussed above when the everting element is inverted.

The everting catheter system 11a includes an everting catheter 17a. The everting catheter 17a does not have the cervical disc 37, the curved distal end portion 35 or the handle 41 of the system 11. The inner body fitting 65a is conventional and the transfer catheter 19 does not have the member 91 and may be conventional. Except for the clip 131, the everting catheter 17a may be conventional.

FIG. 10 shows an everting catheter system 11b which is identical to the everting catheter system 11 in all respects not shown or described herein. Portions of the everting catheter system 11b corresponding to portions of the everting catheter system 11 are designated by corresponding reference numerals followed by the letter b.

Structurally, the systems 11 and 11b may be identical except that the transfer catheter 19 of the system 11 is replaced with a sampling instrument 19b. The sampling instrument 19b may be identical to the transfer catheter 19 except that it is longer in relation to the everting catheter 17b so that with the everting element 29b fully everted, a distal end portion 201 of the sampling instrument 19 lies distally of the distal end 118b of the everting element 29b. The proximal end of the sampling instrument 19b is coupled to a suitable suction source 205, such as a syringe, for applying a subatmospheric pressure to the lumen 87b of the sampling instrument 19b.

The everting catheter 17b may be identical to the everting catheter 17 except that it is sized to access an interior body region, such as a urinary bladder 207, so that a sample can be taken from this interior body region. In addition, the everting catheter 17b does not have the cervical disk 37 and the curved distal end portion 35; however, the catheter 17b can have a configuration suitable for accessing the particular interior body region of interest. Similarly, the sampling instrument 19b is also appropriately sized to take a sample from a desired sampling location.

In use of the everting catheter system 11b, the handle 41b is grasped by the physician and used to position the distal portion of the everting catheter 17b at the opening of the urethra. The inner body fitting 65b is manually advanced within the central passage 59b until the inner body fitting abuts the transverse wall 63b or until some other predetermined longitudinal position is reached. The sampling instrument 19b, which is suitable for urinary sampling is advanced through the inner body fitting 65b to the position shown in FIG. 10 in which the member 91b is retained by the recesses 57b to thereby releasably retain the sampling instrument 19b in a substantially fixed longitudinal position in which the distal end portion 201 of the sampling instrument extends beyond the distal end 118b of the everting element 29b. The suction source 205 is then activated to draw the desired sample which may be fluid or tissue out of the bladder 207 for analysis.

Of course, the procedure described above can be varied as necessary to accommodate particular needs. For example, a material for biopsy could be obtained through the instrument 19b and/or deposition of materials can occur through the instrument 19b. In any event, upon completion of the medical procedure, proximal movement of the inner body fitting 65b to contact the member 91b and dislodge it from the recesses 57b automatically decouples the instrument 19b from the handle 41b. Thus, proximal and distal movement of both the inner body fitting 65b and the instrument 19b are guided by the handled 41b and the longitudinal positioning of these two elements is also facilitated by the handle.

Although exemplary embodiments of the invention have been shown and described, many changes, modifications and substitutions may be made by one having ordinary skill in the art without necessarily departing from the spirit and scope of this invention.

We claim:

1. In an everting catheter useable with an elongated instrument wherein the everting catheter includes an elongated outer tubular body having an outer body lumen and an opening leading from the outer body lumen, an elongated inner tubular body moveable longitudinally in the outer body lumen and having an inner body lumen adapted to receive the instrument, and an everting element coupled to the outer body and the inner body so that with movement of the inner body longitudinally in the outer body lumen the everting element can be everted and inverted, the improvement comprising:

coupling means on the outer body and cooperable with the instrument for retaining the instrument in the inner body lumen in a substantially fixed longitudinal position relative to the outer body.

2. An everting catheter as defined in claim 1 wherein said coupling means includes a clip coupled to the outer body and couplable to the instrument to fix the instrument in said longitudinal position.

3. An everting catheter as defined in claim 1 wherein said coupling means includes an elongated handle coupled to said outer body and an attachment portion on said elongated handle cooperable with the instrument for retaining the instrument in said fixed longitudinal position.

4. In an everting catheter system which includes an elongated outer tubular body having an outer body lumen and an opening leading from the outer body lumen, an elongated inner tubular body moveable longitudinally in the outer body lumen and having an inner body lumen, an everting element coupled to the outer body and the inner body so that with movement of the inner body longitudinally in the outer body lumen the everting element can be everted and inverted, and an elongated instrument moveable longitudinally in the inner body lumen relative to the inner body, the improvement comprising:

a coupling coupled to the outer body for releasably coupling the instrument to the outer body in a substantially fixed longitudinal position with respect to the outer body.

5. An improvement as defined in claim 4 wherein said coupling includes a clip coupled to the outer body and releasably couplable to the instrument.

6. An improvement as defined in claim 4 wherein said coupling includes an elongated handle coupled to the outer body, a releasable attachment portion disposed on the elongated handle, and a releasable attachment portion disposed on the instrument for releasably retaining the instrument in said substantially fixed longitudinal position.

7. An improvement as defined in claim 6 wherein the attachment portion of the elongated handle is at a location along said elongated handle, and said attachment portion on the elongated handle and the attachment portion on the instrument are responsive to the movement of said instrument to bring the attachment portion of said instrument to the attachment portion of said elongated handle to retain the instrument in said substantially fixed longitudinal position.

8. An improvement as defined in claim 6 wherein the elongated handle further includes a longitudinal passage in communication with the outer body lumen, said instrument being receivable in said elongated handle passage.

9. An improvement as defined in claim 8 wherein the elongated handle further includes an elongated longitudinally extending slot and the attachment portion of the instrument is slideable in said slot.

10. An improvement as defined in claim 4 wherein the coupling includes means responsive to movement of the inner body proximally to a predetermined location to decouple and to allow movement of the instrument relative to the outer body.

11. An improvement as defined in claim 4 wherein the coupling includes means responsive to movement of the instrument distally to said substantially fixed longitudinal position to releasably couple the instrument to the outer body in said substantially fixed longitudinal position.

12. An improvement as defined in claim 4 wherein the instrument includes a transfer catheter.

13. An everting catheter comprising:
    an elongated outer tubular body having a proximal end portion, an outer body lumen and a distal opening leading from the outer body lumen;
    an elongated inner tubular body moveable longitudinally in the outer body lumen and having a proximal end portion, an inner body fitting coupled to the proximal end portion of the inner body and an inner body lumen adapted to receive an elongated instrument;
    an everting element coupled to the outer body and the inner body so that with movement of the inner body longitudinally in the outer body lumen the everting element can be everted and inverted;
    an elongated handle coupled to the proximal end portion of the outer body and having a longitudinal handle passage communicating with the outer body lumen; and
    said inner body fitting being slidable longitudinally in the handle passage.

14. An everting catheter as defined in claim 13 wherein the handle has a longitudinal slot.

15. An everting catheter as defined in claim 14 wherein the handle has a proximal end and the slot extends from the proximal end of the handle distally for a major length of the handle.

16. An everting catheter as defined in claim 14 wherein the handle has a distal end, generally opposed surfaces which define said slot and generally opposed recesses in said surfaces, said recesses being spaced proximally from the distal end of the handle.

17. An everting catheter as defined in claim 16 wherein said slot is narrower distally of said recesses than proximally of said recesses.

18. An everting catheter as defined in claim 16 wherein a projecting portion of the inner body fitting projects out of said slot to facilitate manual longitudinal movement of the inner body fitting in said handle passage and said recesses are spaced proximally of the distal end of the handle sufficiently to permit said projecting portion of the inner body fitting along said slot to be located distally of said recesses.

19. An everting catheter as defined in claim 14 including an outer body fitting coupling the handle to the outer body and said handle includes an elongated substantially cylindrical tube having said handle passage and said slot therein.

20. An everting catheter as defined in claim 13 wherein the inner body fitting has a passage communicating with the inner body lumen.

21. An everting catheter as defined in claim 13 wherein the outer body has a distal end portion which is curved.

* * * * *